US00PP36352P3

(12) United States Plant Patent
Schoone

(10) Patent No.: US PP36,352 P3
(45) Date of Patent: Dec. 31, 2024

(54) ***PHALAENOPSIS* PLANT NAMED 'HOT CHILLI'**

(50) Latin Name: *Phalaenopsis hybrida*
Varietal Denomination: Hot Chilli

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,359

(22) Filed: Dec. 3, 2023

(65) Prior Publication Data

US 2024/0188467 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Hot Chilli', characterized by its upright plant habit; moderately vigorous growth habit; strong flowering stems; strong leaves; freely flowering habit with typically two inflorescences developing per plant, each inflorescence with numerous flowers; flowers with dark purplish red-colored petals and sepals; flowers with white, reddish purple and yellow-colored labella; and good postproduction longevity.

2 Drawing Sheets

Figure 1:
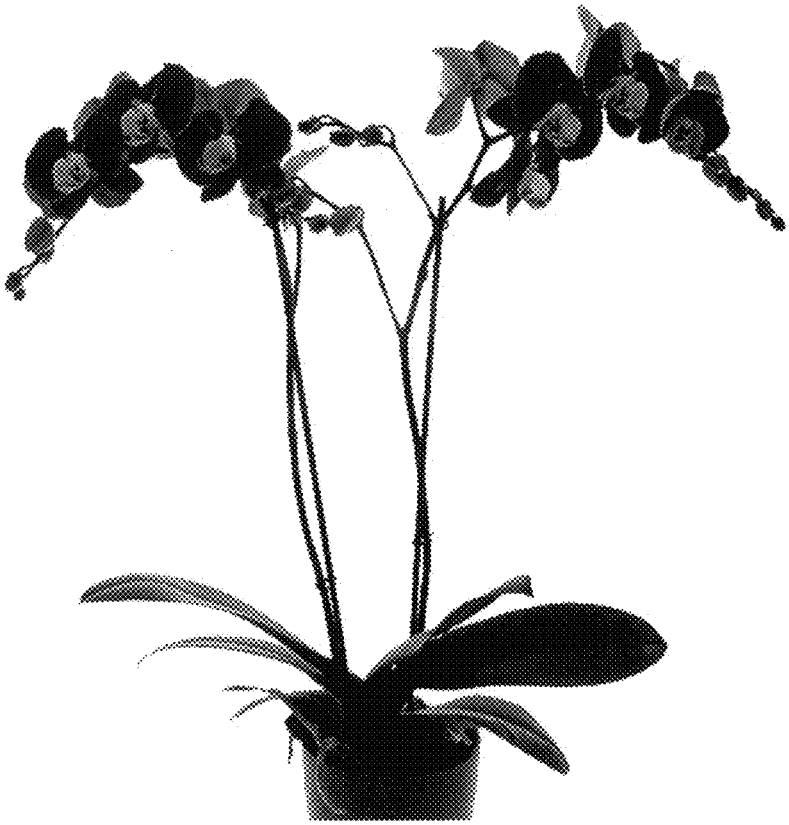

Botanical designation: *Phalaenopsis hybrida.*
Cultivar denomination: 'HOT CHILLI'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Aug. 15, 2022, application number 2022/1913. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Hot Chilli'.

The new *Phalaenopsis* plant is a product of a planned breeding program conducted by the Inventor in De Lier, Heemskerk and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2013 in De Lier, The Netherlands of a proprietary selection of *Phalaenopsis hybrida* identified as code number CX355, not patented, as the female, or seed, parent with a proprietary selection of *Phalaenopsis hybrida* identified as code number 0109100, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2018.

Asexual reproduction of the new *Phalaenopsis* plant by in vitro meristem propagation in a controlled environment in Assendelft, The Netherlands since October 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hot Chilli'. These characteristics in combination distinguish 'Hot Chilli' as a new and distinct *Phalaenopsis* plant:

1. Upright plant habit.
2. Moderately vigorous growth habit.
3. Strong flowering stems.
4. Strong leaves.
5. Freely flowering habit with typically two inflorescences developing per plant, each inflorescence with numerous flowers.
6. Flowers with dark purplish red-colored petals and sepals.
7. Flowers with white, reddish purple and yellow-colored labella.
8. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals and sepals of plants of the new *Phalaenopsis* are dark purplish red in color whereas flower petals and sepals of plants of the female parent selection are soft violet in color.
2. Flower petals of plants of the new *Phalaenopsis* have a few stripes and no dots whereas flower petals of plants of the female parent selection have a moderate amount of stripes and dots.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* are not imbricate whereas flower petals of plants of the male parent selection are very close to imbricate.
2. Labella of the plants of the new *Phalaenopsis* are white, reddish purple and yellow in color whereas labella of plants of the male parent selection are solid purplish red in color.

Plants of the new *Phalaenopsis* can be compared to plants of x *Doritaenopis* (*Doritis* X *Phalaenopsis*) 'Bulls Eye', disclosed in U.S. Plant Pat. No. 34,645. In side-by-side comparisons, plants of the new *Phalaenopsis* differ primarily from plants of 'Bulls Eye' in the flower color as labella of the plants of the new *Phalaenopsis* are white, reddish purple and yellow in color whereas labella of plants of 'Bulls Eye' are solid purple in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Hot Chilli' grown in a container.

Figure 2:
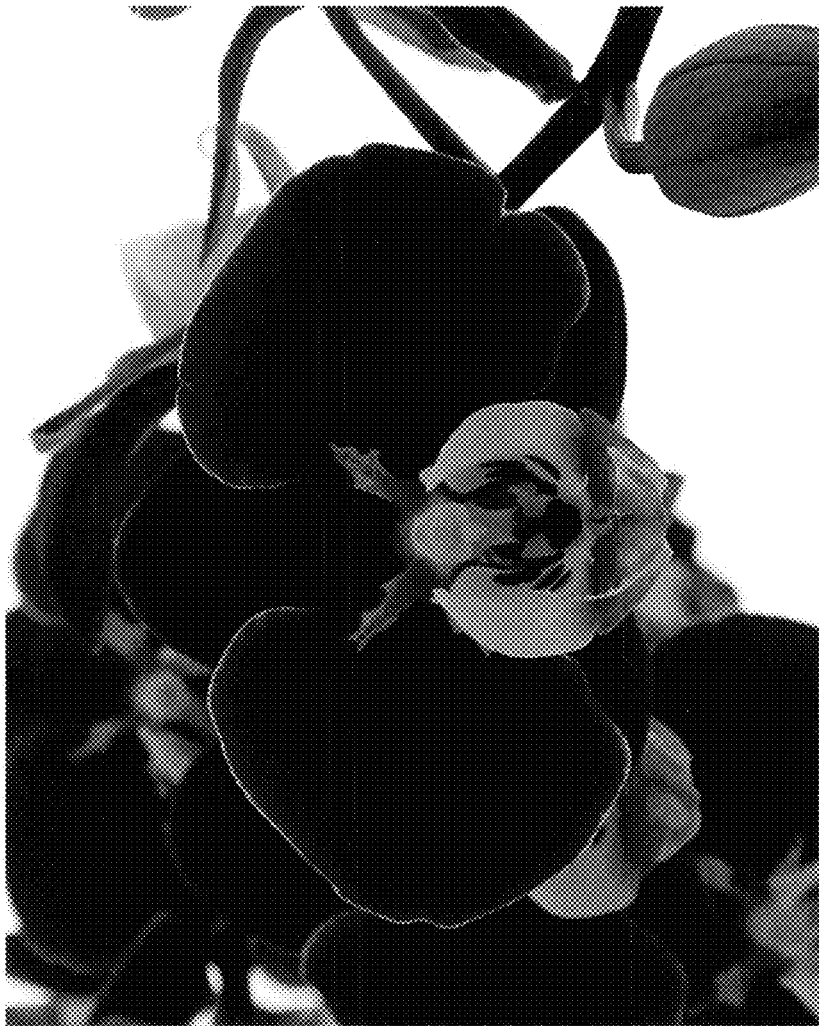

The photograph on the second sheet (FIG. 2) is a close-up view of a typical flower bud and a typical flower of 'Hot Chilli'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Hot Chilli'.

Parentage:

*Female, or seed, parent*.—Proprietary selection of *Phalaenopsis hybrida* identified as code number CX355, not patented.

*Male, or pollen, parent*.—Proprietary selection of *Phalaenopsis hybrida* identified as code number 0109100, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 16.2 cm.

*Plant height, substrate level to top of floral plane*.—About 49 cm.

*Plant diameter or spread*.—About 34.1 cm.

Leaf description:

*Arrangement and quantity*.—Distichous, simple; sessile; about four fully-developed leaves per plant.

*Length*.—About 22.7 cm.

*Width*.—About 6.7 cm.

*Aspect*.—Semi-erect to horizontal and eventually outwardly arching.

*Shape*.—Narrowly oblong; slightly carinate.

*Apex*.—Unequal and broadly acute to unequal obtuse.

*Base*.—Sheathing. Sheath length: About 1.9 cm. Sheath width: About 1.5 cm. Sheath color: Close to 148A and 148B and towards the margins, strongly tinged with close to 200B and 200C.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B. Developing leaves, lower surface: Close to 146A strongly tinged with close to N77A. Fully expanded leaves, upper surface: Close to NN137B; venation, close to NN137A. Fully expanded leaves, lower surface: Close to 146A; towards the margins and apex, slightly tinged with close to N77A; venation, close to 144A.

Inflorescence description:

*Appearance and flowering habit*.—Showy zygomorphic flowers arranged on axillary simple or branched racemes; typically two inflorescences develop per plant; each inflorescence with about 15 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 28.7 cm.

*Inflorescence width*.—About 15.7 cm.

*Flower buds*.—Height: About 2 cm. Diameter: About 1.4 cm by 1.7 cm. Shape: Broadly ovate. Color: Close to a blend of 152B, 152C and 152D; towards the apex, tinged with close to 71A.

*Flower size*.—About 7.5 cm (vertical) by 8.4 cm (horizontal).

*Flower depth*.—About 4.2 cm.

*Petals, quantity and arrangement*.—Three, two lateral petals and one center petal transformed into a labellum.

*Lateral petals*.—Length: About 3.9 cm. Width: About 4.9 cm. Shape: Broadly reniform to close to lunate. Apex: Shallowly retuse. Margin: Entire; not undulate. Texture and luster, upper and lower surfaces: Smooth, glabrous, velvety; matte. Color: When opening, upper surface: Close to a blend of 59A and 187C with a few fine dots, close to 200B; at the base, blotched and with a few fine dots, close to 72B and 187C. When opening, lower surface: Slightly lighter than a blend of 76A and N187D; towards the base, close to 76C and at the base, close to 157A; venation, close to N75A. Fully opened, upper surface: Close to a blend of 71A and N79C; towards the base, close to 59A and at the base, close to NN155D with irregular blotching, close to N78A; color does not change with subsequent development. Fully opened, lower surface: Close to a blend of 76A and N187D; towards the base, close to 59A and at the base, close to NN155D with irregular blotching, close to N78A; color does not change with subsequent development.

*Labella*.—Appearance: Three-parted with two lateral lobes and a central lobe. Length, lateral lobes: About 2.2 cm. Width, lateral lobes: About 1.7 cm. Length, central lobe: About 2.1 cm. Width, central lobe: About 6 mm to 24 mm. Length, cirrhose tips: About 1.3 cm. Shape, lateral lobes: Obovate to close to rhomboid. Shape, central lobe: Deltoid with a slightly elongated apex. Apex, lateral lobes: Obtuse. Apex, central lobe: Cleft with two reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 6 mm in width and about 5 mm in height. Color: When opening, upper surface: Lateral lobes: Close to NN155D; towards the base, fine dots, close to 59A and 187B; proximal margins, close to 4C with marginal edges, close to 59C. Central lobe: Close to NN155D; towards the base, tinged with close to 60C and at the base, close to N186C; towards the apex, tinged with close to N78C and N78D; midvein, close to NN78B; cirrhose tips, close to NN155D with dots, close to N78C. Callosities: Close to N186C; towards the apex, close to 4D and towards the margins, close to NN155B. When opening, lower surface: Lateral lobes: Close to 155C tinged with close to 76A and 76B; proximal margins, close to 4C strongly tinged with close to 60A. Central lobe: Close to N78D; towards the apex and cirrhose tips, close to N78C; apical margins, close to 60B; at the base, close to 155C. Fully opened, upper surface: Lateral lobes: Close to NN155D slightly tinged with close to 76C; towards the base, fine dots, close to 59A and 187B; proximal margins, close to 4C to 4D with marginal edges, close to 59C to 59D. Central lobe: Close to NN155D; towards the base, tinged with close to 60C and at the base, close to N186C; towards the apex, tinged with close to N78C and N78D; midvein, close to NN78A to NN78B; cirrhose tips, close to 75D with dots, close to N78C. Callosities: Inner surface, close to 187A; outer surface, close to NN155B with apex, close to 2B. Fully opened, lower surface: Lateral lobes: Close to 155C tinged with close to 76A; proximal margins, close to 4C strongly tinged with close to 60A. Central lobe: Close to N78D; towards the apex and cirrhose tips, close to N78C; apical margins, close to 60B; at the base, close to 155C.

*Sepals*.—Quantity and arrangement: Three, one upper dorsal sepal and two lower lateral sepals. Length, dorsal sepal: About 4.1 cm. Width, dorsal sepal: About 3 cm. Length, lateral sepals: About 4.2 cm. Width, lateral sepals: About 2.7 cm. Shape, dorsal sepal: Elliptic. Shape, lateral sepals: Ovate to elliptic. Apex, dorsal and lateral sepals: Broadly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to a blend of 59A and 187C; venation, close to 187A. When opening, lower surface: Close to a blend of N148A and 152D; towards the apex, slightly tinged with close to N77B; venation, close to N199A. Fully opened, upper surface: Close to a blend of 71A and N79C; center, close to 59A; venation, close to 187A; color does not change with subsequent development. Fully opened, lower surface: Close to 76A; towards the base, close to 76C; venation, close to N75A; color does not change with subsequent development. Color, lateral sepals: When opening, upper surface: Close to a blend of 59A, 187C and 187D; towards the base, close to N186C; venation, close to 187A. When opening, lower surface: Close to a blend of N148A and 152D; towards the apex, slightly tinged with close to N77B; venation, close to N199A. Fully opened, upper surface: Close to a blend of 71A and N79C; center, close to 59A; venation, close to 187A; color does not change with subsequent development. Fully opened, lower surface: Close to 76A; towards the base, strongly tinged with close to N148D; midvein, distally, close to N78A and lateral venation, close to N75A; color does not change with subsequent development.

*Peduncles*.—Length: About 58.5 cm. Diameter: About 5.5 mm. Strength: Strong. Aspect: Upright to outwardly arching. Texture and luster: Smooth, glabrous; matte. Color: Close to N200A; dense fine dots and marbling, close to 148D.

*Pedicels*.—Length: About 3.8 cm. Diameter: About 3.5 mm. Strength: Moderately strong. Aspect: About 40 degrees from peduncle axis. Texture and luster: Smooth, glabrous; matte. Color: Close to 146D; proximally, close to N79B and distally, close to 75A to 75B.

*Reproductive organs*.—Androecium: Column length: About 9 mm. Column width: About 6 mm. Column color: Close to NN155D slightly tinged with close to N75D. Pollinia quantity: Two. Pollinia diameter (per two pollinia): About 2.5 mm. Pollinia color: Close to 24A. Gynoecium: Stigma length: About 3 mm. Stigma width: About 4 mm. Stigma shape: Reniform. Stigma color: Close to N155D. Ovary length: About 1 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Hot Chilli' as illustrated and described.

* * * * *